United States Patent [19]

Rostami et al.

[11] Patent Number: 6,039,902
[45] Date of Patent: Mar. 21, 2000

[54] METHODS OF RECYCLING CATALYST IN OXIDATIONS OF HYDROCARBONS

[75] Inventors: Ader M. Rostami, Bainbridge Island; David C. DeCoster, Buckley, both of Wash.; Eustathios Vassiliou, Newark, Del.; Mark W. Dassel, Indianola, Wash.

[73] Assignee: RPC Inc., Atlanta, Ga.

[21] Appl. No.: 08/932,875

[22] Filed: Sep. 18, 1997

Related U.S. Application Data

[63] Continuation-in-part of application No. 08/931,035, Sep. 16, 1997, which is a continuation-in-part of application No. 08/876,692, Jun. 16, 1997, which is a continuation-in-part of application No. 08/812,847, Mar. 6, 1997, and application No. 08/824,992, Mar. 27, 1997, Pat. No. 5,922,908.
[60] Provisional application No. 60/020,798, Jun. 24, 1996.

[51] Int. Cl.$^7$ .............................. C07C 51/42; D01D 1/02; D01D 5/08; D01F 13/00
[52] U.S. Cl. .................................. 264/37.18; 264/37.26; 264/176.1; 528/176; 528/288; 528/308; 528/322; 528/335; 562/543
[58] Field of Search .......................... 264/37.18, 37.26, 264/176.1; 528/176, 288, 308, 322, 335; 562/543

[56] References Cited

U.S. PATENT DOCUMENTS

| | | |
|---|---|---|
| 1,121,532 | 12/1914 | Newberry . |
| 2,014,044 | 9/1935 | Haswell ........................ 75/17 |
| 2,223,493 | 12/1940 | Loder ........................ 260/537 |
| 2,223,494 | 12/1940 | Loder ........................ 260/586 |
| 2,301,240 | 11/1942 | Baumann et al. ........................ 183/115 |
| 2,439,513 | 4/1948 | Hamblet et al. ........................ 260/533 |
| 2,557,282 | 6/1951 | Hamblet et al. ........................ 260/533 |
| 2,565,087 | 8/1951 | Porter et al. ........................ 260/631 |
| 2,980,523 | 4/1961 | Dille et al. ........................ 48/215 |
| 3,161,603 | 12/1964 | Leyshon et al. ........................ 252/413 |
| 3,231,608 | 1/1966 | Kollar ........................ 260/533 |
| 3,234,271 | 2/1966 | Barker et al. ........................ 260/531 |
| 3,290,369 | 12/1966 | Bonfield et al. ........................ 260/537 |
| 3,361,806 | 1/1968 | Lidov ........................ 260/531 |
| 3,515,751 | 6/1970 | Oberster et al. ........................ 260/533 |
| 3,530,185 | 9/1970 | Pugi ........................ 260/586 |
| 3,613,333 | 10/1971 | Gardenier ........................ 55/89 |
| 3,677,696 | 7/1972 | Bryk et al. ........................ 23/2 |
| 3,839,435 | 10/1974 | Motoo Shigeyasu et al. ..... 260/524 R |
| 3,928,005 | 12/1975 | Laslo ........................ 55/73 |
| 3,932,513 | 1/1976 | Russell ........................ 260/586 |
| 3,946,076 | 3/1976 | Paasen et al. ........................ 260/586 |
| 3,957,876 | 5/1976 | Rapoport et al. ........................ 260/586 |
| 3,987,100 | 10/1976 | Barnette et al. ........................ 260/586 |
| 3,987,808 | 10/1976 | Carbonell et al. ........................ 137/3 |
| 4,025,498 | 5/1977 | Buss et al. ........................ 260/95 A |
| 4,039,304 | 8/1977 | Bechthold et al. ........................ 55/10 |
| 4,055,600 | 10/1977 | Langley et al. ........................ 260/586 |
| 4,065,527 | 12/1977 | Graber ........................ 261/79 A |
| 4,308,037 | 12/1981 | Meissner et al. ........................ 55/10 |
| 4,332,590 | 6/1982 | Smith ........................ 23/230 A |
| 4,361,965 | 12/1982 | Goumondy et al. ........................ 34/57 |
| 4,370,304 | 1/1983 | Hendriks et al. ........................ 422/224 |
| 4,394,139 | 7/1983 | Board ........................ 55/20 |
| 4,419,184 | 12/1983 | Backlund ........................ 162/49 |
| 4,423,018 | 12/1983 | Lester, Jr. et al. ........................ 423/243 |
| 5,061,453 | 10/1991 | Krippl et al. ........................ 422/106 |
| 5,104,492 | 4/1992 | King et al. ........................ 203/15 |
| 5,123,936 | 6/1992 | Stone et al. ........................ 55/8 |
| 5,170,727 | 12/1992 | Nielsen ........................ 110/346 |
| 5,221,800 | 6/1993 | Park et al. ........................ 562/543 |
| 5,244,603 | 9/1993 | Davis ........................ 261/87 |

(List continued on next page.)

FOREIGN PATENT DOCUMENTS

| | | |
|---|---|---|
| 439 007 A2 | 7/1991 | European Pat. Off. . |
| 729 084 A1 | 8/1996 | European Pat. Off. . |
| 729 085 A1 | 8/1996 | European Pat. Off. . |
| 751 105 A2 | 1/1997 | European Pat. Off. . |
| 2 722 783 A1 | 1/1996 | France . |
| 4426132A1 | 1/1996 | Germany . |
| 4427474 A1 | 2/1996 | Germany . |
| 48-003815 | 2/1973 | Japan . |
| 415172 | 8/1934 | United Kingdom . |
| 738808 | 10/1955 | United Kingdom . |
| 864106 | 3/1961 | United Kingdom . |
| 1143213 | 2/1969 | United Kingdom . |
| 2014473 | 8/1979 | United Kingdom . |
| 2 072 667 | 10/1981 | United Kingdom . |
| WO96/03365 | 2/1996 | WIPO . |
| WO 96/40610 | 12/1996 | WIPO . |
| WO 97/49485 | 12/1997 | WIPO . |

OTHER PUBLICATIONS

U.S. application 08/587,967, filed Jan. 17, 1996.
U.S. application 08/812,847, filed Mar. 6, 1997.
U.S. application 08/859,985, filed May 21, 1997.
U.S. application 08/861,281, filed May 21, 1997.
U.S. application 08/861,180, filed May 21, 1997.
U.S. application 08/861,176, filed May 21, 1997.
U.S. application 08/859,890, filed May 21, 1997.
U.S. application 08/861,210, filed May 21, 1997.
U.S. application 08/824,992, filed Mar. 27, 1997.
U.S. application 08/477,195, filed Jun. 7, 1995.
U.S. application 08/876,692, filed Jun. 16, 1997.
U.S. application 08/900,323, filed Jul. 25, 1997.
U.S. application 08/931,035, filed Sep. 16, 1997.
E. Sorribes et al., "Formación de neuvas fases en el proceso de obtención de ácido adípico: causas y efectos que provocan," *Rev. R. Acad. Cienc. Exactas, Fis. Nat. Madrid* (1987), 81 (1), 233–5 (+English language translation).

*Primary Examiner*—Leo B. Tentoni
*Attorney, Agent, or Firm*—Seed Intellectual Property Law Group PLLC

[57] ABSTRACT

This invention relates to methods of recycling catalyst in oxidations of hydrocarbons, such as cyclohexane for example, to respective intermediate oxidation products, such as adipic acid for example, by a direct process. The catalyst remains in solution despite removal of water from the composition, since the water removal is controlled at such temperatures and such remaining water levels that prevent catalyst from precipitating. The water removal is preferably conducted before removal of the intermediate oxidation product. Also, preferably, some, and more preferably all steps of the process are conducted in a single liquid phase region.

38 Claims, 2 Drawing Sheets

U.S. PATENT DOCUMENTS

| | | | |
|---|---|---|---|
| 5,270,019 | 12/1993 | Melton et al. | 422/234 |
| 5,271,904 | 12/1993 | Esposito et al. | 422/105 |
| 5,286,458 | 2/1994 | Yang et al. | 422/168 |
| 5,294,378 | 3/1994 | Succi et al. | 261/130 |
| 5,312,567 | 5/1994 | Kozma et al. | 261/87 |
| 5,321,157 | 6/1994 | Kollar | 562/543 |
| 5,374,767 | 12/1994 | Drinkard et al. | 560/193 |
| 5,396,850 | 3/1995 | Conochie et al. | 110/346 |
| 5,399,750 | 3/1995 | Brun et al. | 562/553 |
| 5,463,119 | 10/1995 | Kollar | 562/543 |
| 5,502,245 | 3/1996 | Dassel et al. | 562/413 |
| 5,516,423 | 5/1996 | Conoby et al. | 210/85 |
| 5,558,842 | 9/1996 | Vassiliou et al. | 422/108 |
| 5,580,531 | 12/1996 | Vassiliou et al. | 422/108 |
| 5,654,475 | 8/1997 | Vassiliou et al. | 562/413 |
| 5,756,837 | 5/1998 | Costantini et al. | 562/543 |

METHODS OF RECYCLING CATALYST IN OXIDATIONS OF HYDROCARBONS

CROSS-REFERENCES TO RELATED APPLICATIONS

This application is a continuation-in-part of U.S. patent application Ser. No. 08/931,035, filed on Sep. 16, 1997, of Mark W. Dassel, Ader M. Rostami, David C. DeCoster, and Eustathios Vassiliou, which is a continuation-in-part of U.S. patent application Ser. No. 08/876,692, filed on Jun. 16, 1997, of Ader M. Rostami, David C. DeCoster, Eustathios Vassiliou, Mark W. Dassel, and Sharon M. Aldrich, which in turn is a continuation-in-part of U.S. patent application Ser. No. 08/812,847, filed on Mar. 6, 1997, which in turn claims priority of Provisional Application No. 60/020,798, filed on Jun. 24, 1996; and which U.S. patent application Ser. No. 08/876,692 is also a continuation-in-part of U.S. patent application Ser. No. 08/824,992, filed Mar. 27, 1997 (now U.S. Pat. No. 5,922,908, issued Jul. 13, 1999); all of which are incorporated herein by reference.

TECHNICAL FIELD

This invention relates to methods of recycling catalyst in oxidations of hydrocarbons, such as cyclohexane for example, to respective intermediate oxidation products, such as adipic acid for example, by a direct process.

BACKGROUND OF THE INVENTION

There is a plethora of references (both patents and literature articles) dealing with the formation of acids, one of the most important being adipic acid, by oxidation of hydrocarbons. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process," the "Boric Acid Process," and the "Direct Synthesis Process," which involves direct oxidation of cyclohexane to adipic acid with oxygen in the presence of solvents, catalysts, and promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar Phase" and the "Non-Polar Phase." However, no attention has been paid so far to the importance of the two phases, except for separating the adipic acid from the "Polar Phase" and recycling these phases to the reactor partially or totally with or without further treatment.

It is also important to note that most studies on the Direct Oxidation have been conducted in a batch mode, literally or for all practical purposes.

There is a plethora of references dealing with oxidation of organic compounds to produce acids, such as, for example, adipic acid and/or intermediate products, such as for example cyclohexanone, cyclohexanol, cyclohexylhydroperoxide, etc.

The following references, among the plethora of others, may be considered as representative of oxidation processes relative to the preparation of diacids and other intermediate oxidation products.

U.S. Pat. No. 5,463,119 (Kollar) discloses a process for the oxidative preparation of $C_5$–$C_8$ aliphatic dibasic acids by
(1) reacting,
  (a) at least one saturated cycloaliphatic hydrocarbon having from 5 to 8 ring carbon atoms in the liquid phase and
  (b) an excess of oxygen gas or an oxygen-containing gas in the presence of
  (c) a solvent comprising an organic acid containing only primary and/or secondary hydrogen atoms and
  (d) at least about 0.002 mole per 1000 grams of reaction mixture of a polyvalent heavy metal catalyst;
(2) removing the aliphatic dibasic acid; and
(3) recycling intermediates, post oxidation components, and derivatives thereof remaining after removal of the aliphatic dibasic acid into the oxidation reaction.

U.S. Pat. No. 5,374,767 (Drinkard et al.) discloses formation of cyclohexyladipates in a staged reactor, e.g., a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of $C_5$–$C_8$ aliphatic dibasic acids through oxidation of corresponding saturated cycloaliphatic hydrocarbons by
(1) reacting, at a cycloaliphatic hydrocarbon conversion level of between about 7% and about 30%,
  (a) at least one saturated cycloaliphatic hydrocarbon having from 5 to 8 ring carbon atoms in the liquid phase and
  (b) an excess of oxygen gas or an oxygen containing gas mixture in the presence of
  (c) less than 1.5 moles of a solvent per mole of cycloaliphatic hydrocarbon (a), wherein said solvent comprises an organic acid containing only primary and/or secondary hydrogen atoms and
  (d) at least about 0.002 mole per 1000 grams of reaction mixture of a polyvalent heavy metal catalyst; and
(2) isolating the C5–C8 aliphatic dibasic acid.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Oberster et al.) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al.) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al.) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al.) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al.) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al.) discloses production of adipic acid and related aliphatic dibasic acids; more particularly to the production of adipic acid by the direct oxidation of cyclohexane.

U.S. Pat. No. 2,439,513 (Hamblet et al.) discloses the production of adipic acid and related aliphatic dibasic acids and more particularly to the production of adipic acid by the oxidation of cyclohexane.

U.S. Pat. No. 2,223,494 (Loder et al.) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al.) discloses the production of aliphatic dibasic acids and more particularly to the production of aliphatic dibasic acids by oxidation of cyclic saturated hydrocarbons with an oxygen-containing gas.

German Patent DE 44 26 132 A1 (Kysela et al.) discloses a method of dehydration of process acetic acid from liquid-phase oxidation of cyclohexane with air, in the presence of cobalt salts as a catalyst after separation of the adipic acid after filtration, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than [sic] 0.3–0.7%.

PCT International Publication WO 96/03365 (Constantini et al.) discloses a process for recycling a cobalt-containing catalyst in a direct reaction of oxidation of cyclohexane into adipic acid, characterized by including a step in which the reaction mixture obtained by oxidation into adipic acid is treated by extraction of at least a portion of the glutaric acid and the succinic acid formed during the reaction.

The patent literature is inconsistent and at least confusing regarding addition or removal of water in oxidations. For example:

U.S. Pat. No. 5,221,800 (Park et al.) discloses a process for the manufacture of adipic acid. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 4,263,453 (Schultz et al.) discloses a process claiming improved yields by the addition of water at the beginning of the reaction, generally of the order of 0.5 to 15% relative to monobasic aliphatic acid solvent, and preferably 1 to 10% relative to the solvent.

U.S. Pat. No. 3,390,174 (Schultz et al.) discloses a process claiming improved yields of aliphatic dibasic acids when oxidizing the respective cyclic hydrocarbons at temperatures between 130° and 160° C., while removing the water of reaction substantially as quickly as it is formed.

None of the above references, or any other references known to the inventors disclose, suggest or imply, singly or in combination, control of oxidation reactions by adjusting the water level subject to the intricate and critical controls and requirements of the instant invention as described and claimed.

Our U.S. Pat. Nos. 5,580,531, 5,558,842, 5,502,245, and our co-pending applications Ser. Nos. 08/477,195 (filed Jan. 7, 1995), 08/587,967 (filed Jun. 17, 1996), and 08/620,974 (filed Mar. 25, 1996), all of which are incorporated herein by reference, describe methods and apparatuses relative to controlling reactions in atomized liquids. Our co-pending application, Docket No. T-603, Ser. No 08/812,847, filed on Mar. 6, 1997, and our co-pending application, Docket No. T-701, Ser. No. 08/824,992, filed on Mar. 27, 1997, are both also incorporated herein by reference.

All of the following patent applications, which were filed simultaneously on May 21, 1997, are also incorporated herein by reference:

U.S. pat. application Ser. No. 08/859,985 of Eustathios Vassiliou, Mark W. Dassel, David C. DeCoster, Ader M. Rostami, and Sharon M. Aldrich, titled "Methods and Devices for Controlling the Reaction Rate of a Hydrocarbon to an Intermediate Oxidation Product by Pressure Drop Adjustments";

U.S. patent application Ser. No. 08/861,281 of Mark W. Dassel, Eustathios Vassiliou, David C. DeCoster, Ader M. Rostami, and Sharon M. Aldrich, titled "Methods and Devices for Controlling the Reaction Rate of a Hydrocarbon to an Intermediate Oxidation Product by Monitoring Flow of Incoming and Outcoming Gases";

U.S. patent application Ser. No. 08/861,180 of David C. DeCoster, Ader M. Rostami, Mark W. Dassel, and Eustathios Vassiliou, titled "Methods and Devices for Controlling the Oxidation Rate of a Hydrocarbon by Adjusting the Ratio of the Hydrocarbon to a Rate-Modulator";

U.S. patent application Ser. No. 08/861,176 of Mark W. Dassel, Eustathios Vassiliou, David C. DeCoster, and Ader M. Rostami, titled "Methods of Preparing an Intermediate Oxidation Product from a Hydrocarbon by Utilizing an Activated Initiator";

U.S. patent application Ser. No. 08/859,890 of Ader M. Rostami, Mark W. Dassel, Eustathios Vassiliou, David C. DeCoster, titled "Methods and Devices for Controlling the Oxidation of a Hydrocarbon to an Acid by Regulating Temperature/Conversion Relationship in Multi-Stage Arrangements"; and U.S. patent application Ser. No. 08/861,210 of Eustathios Vassiliou, Ader M. Rostami, David C. DeCoster, and Mark W. Dassel, titled "Pseudo-Plug-Flow Reactor."

Further, our U.S. patent application Ser. No. 08/876,692 filed on Jun. 16, 1997, of Ader M. Rostami, David C. DeCoster, Eustathios Vassiliou, Mark W. Dassel, and Sharon M. Aldrich, titled "Methods and Devices for Controlling Hydrocarbon Oxidations to Respective Acids by Adjusting the Water Level during the Reaction" is also incorporated herein by reference.

Our PCT patent application No. PCT/US97/10830, filed on Jun. 23, 1997, of Mark W. Dassel, David C. DeCoster, Ader M. Rostami, Eustathios Vassiliou, and Sharon M. Aldrich, titled "Methods and Devices for Oxidizing a Hydrocarbon to Form an Acid" is incorporated herein by reference.

Also, our PCT patent application No. PCT/US97/12944, filed on Jul. 23, 1997, of David C. DeCoster, Eustathios Vassiliou, Mark W. Dassel, Sharon M. Aldrich, and Ader M. Rostami, titled "Methods and Devices for Controlling the Reaction Rate and/or Reactivity of Hydrocarbon to an Intermediate Oxidation Product by Adjusting the Oxidant Consumption Rate" is also incorporated herein by reference.

In addition, our patent application having U.S. application Ser. No. 08/900,323, filed on Jun. 25, 1997, of Eustathios Vassiliou, Mark W. Dassel, Sharon M. Aldrich, Ader M. Rostami, and David C. DeCoster, titled "Methods and Devices for Controlling Hydrocarbon Oxidations to Respective Acids by Adjusting the Solvent to Hydrocarbon ratio" is also incorporated herein by reference.

Our patent application having U.S. application Ser. No. 08/931,035, filed on Sep. 16, 1997, of Mark W. Dassel, Ader M. Rostami, David C. DeCoster, and Eustathios Vassiliou titled "Methods and Reactor Devices for Removing Catalyst after Oxidation of Hydrocarbons" is also incorporated herein by reference.

SUMMARY OF THE INVENTION

As aforementioned, this invention relates to methods of recycling catalyst in oxidations of hydrocarbons, such as cyclohexane for example, to respective intermediate oxidation products, such as adipic acid for example, by a direct process. It relates particularly to a method of maintaining catalyst in solution after water removal, outside a reaction zone, in a process comprising oxidation of a hydrocarbon by a gaseous oxidant to a respective intermediate oxidation product at an operation temperature in the reaction zone containing a mixture comprising the hydrocarbon, the catalyst, the water, a solvent, and an optional initiator, the method comprising sequential steps of:

(a) changing, outside the reaction zone, the operation temperature of the mixture to a second temperature below a precipitation temperature, at which and over which precipitation temperature, the catalyst in the first mixture would precipitate, at least partially, if the water level in the first mixture had been reduced to or under a precipitation water level;

(b) removing an amount of water from the first mixture, but maintaining the water level in the mixture over the precipitation water level at the second temperature;

(c) removing at least part of the intermediate oxidation product; and (d) re-circulating the remaining mixture to the reaction zone.

It is preferable that all steps are conducted at a substantially single liquid phase region.

Step (b) of the method may comprise a step of lowering the second temperature to a third temperature lower than the second temperature, and step (c) may comprise a step selected from a group consisting of centrifuging, filtering, and a combination thereof. Further, step (a) may comprise a step of atomizing the first mixture.

This invention further pertains a method of maintaining catalyst in solution for recycling after water removal, outside a reaction zone, in a process comprising oxidation of a hydrocarbon by a gaseous oxidant to a respective intermediate oxidation product at an operation temperature in the reaction zone containing a mixture comprising the hydrocarbon, the catalyst, the water, a solvent, and an optional initiator, the method comprising steps of:

(e) precipitating at least partially the intermediate oxidation product, while maintaining a single liquid phase;

(f) removing at least part of the precipitated intermediate oxidation product;

(g) removing part of the water at a temperature below a precipitation temperature, at which and over which precipitation temperature, the catalyst in the mixture would precipitate, at least partially, if the water level in the mixture had been reduced to or under a precipitation water level;

(h) maintaining the water level over the precipitation water level; and (i) recycling at least part of a mixture created in step (h) back to the reaction zone.

This invention is particularly applicable in the case that the intermediate oxidation product comprises adipic acid, the hydrocarbon comprises cyclohexane, the catalyst comprises a cobalt compound, the gaseous oxidant comprises oxygen, the solvent comprises acetic acid, and the optional initiator is selected from a group comprising cyclohexanone, cyclohexylhydroperoxide, acetaldehyde, and a mixture thereof.

Further, the instant invention pertains to a method, wherein the intermediate oxidation product comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

The method may further comprise a step of spinning the polymer into fibers.

It should be noted that reaction products, by-products, and other compounds in the mixture, influence the catalyst precipitation temperature and the precipitation water level. According to this invention, the catalyst precipitation temperature and the precipitation water level are considered in the presence of such moieties in the mixture.

By the term "steady state" it is meant that the reaction has reached an equilibrium, which equilibrium, however, may be adjusted periodically or continuously in order to achieve a desired result. If for example more water is needed in the reaction zone to avoid catalyst precipitation, the water feed rate to the reaction zone may be increased appropriately, and still the reaction may be considered to be at a "steady state." Similarly, if less water is needed to avoid formation of two phases, the water feed rate to the reaction zone may be decreased appropriately, and still the reaction may be considered to be at a "steady state."

The terms "substantially single-phase liquid" and "substantially single liquid phase" are for all practical purposes synonymous for the purposes of this invention. They both intend to indicate that there is no second liquid phase present, while a solid phase may or may not be present. The terms "second phase formation" or "formation of a second phase" refer to a second liquid phase, and not to a solid phase, unless otherwise specified.

The term "level" of an ingredient (reactant, reaction product, catalyst, water, inert matter, or any other type of matter present) includes both "relative level" and "percentage level." According to the instant invention, both methods and devices may perform by using either one or the other type of "levels." In some occasions it may be easier to use one type rather than the other. "Relative level" of an ingredient denotes the amount of the ingredient present in weight units or in volume units, in a reaction zone or in a cell for example, as compared to 100 units, in weight units or in volume units, respectively, of the rest of the ingredients present, or the rest of the ingredients under consideration. The rest of the ingredients present or the rest of the ingredients under consideration, in this case, have a constant ratio with respect to each other. On the other hand, "percentage level" is the level expressed as a percentage based on total amount of all or of a desired number of specific ingredients. The percentages may be expressed also either by weight or by volume.

A controller, preferably a computerized controller, may handle with ease and accuracy either type of "level." Programming a computerized controller to perform such functions is a routine process, well known to the art. According to this invention, a controller, based on information received, from a reaction zone for example, controls feed rates, temperatures, pressures, and other parameters in order to achieve the desirable results. The controller may also be programmed, by techniques well known to the art, to include flow sheet simulation, which may account for vapor/liquid equilibrium and energy balance effects.

Analytical techniques known to the art may be used for determination of levels of the different ingredients in the miscellaneous streams and chambers, and provide such information to the controller for further processing and action.

BRIEF DESCRIPTION OF THE DRAWINGS

The reader's understanding of this invention will be enhanced by reference to the following detailed description taken in combination with the drawing figure, wherein.

DETAILED DESCRIPTION OF THE INVENTION

As aforementioned, this invention relates to methods of recycling catalyst in oxidations of hydrocarbons, such as cyclohexane for example, to respective intermediate oxidation products, such as adipic acid for example, by a direct process.

Proper catalyst handling in oxidation reactions has always been a considerable problem in the art. According to the present invention, the process is controlled in a way that water is removed from the system, while catalyst remains in solution for direct recycling or recycling after any desired treatment. This presents enormous advantages, because the catalyst may be easily and efficiently recycled for repeated utilization.

As aforementioned, German Patent DE 44 26 132 A1 (Kysela et al.) discloses a method of dehydration of process acetic acid from liquid-phase oxidation of cyclohexane with air, in the presence of cobalt salts as a catalyst after separation of the adipic acid after filtration, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of 0.3–0.7%.

The above disclosure does not realize that depending on the level of the catalyst or other ingredients in the composition, these water limits may change drastically, and that it is important to examine in each individual case the water level at which the catalyst precipitates and thus stay above this water level. In addition, the disclosure does not realize that the temperature, at which a mixture containing catalyst is maintained, also drastically changes the water level under which catalyst precipitates.

According to the instant invention, both the temperature of the mixture containing the catalyst, and the water level are controlled in coordination, for a predetermined level of catalyst, so that the catalyst remains in solution, in the presence of other moieties, such as products, by-products, etc. In the case that it is desirable to remove the maximum amount of water from the system, the critical water level, at which catalyst precipitates, is determined at the temperature of the mixture containing the catalyst, and the water level is kept above, but close to the critical level. It is preferable that the water level is maintained in a range of 10% to 100% of the critical value, above the critical value. It is more preferable that the water level is maintained in a range of 20% to 50% of the critical value, above the critical value. For example, if the critical water level value (precipitation water level) at the temperature of the mixture containing the catalyst is 0.6% by weight (based on the total mixture containing the catalyst), it is preferable that the water level is maintained in the range of 0.66% to 1.2% by weight, and more preferably, in the range of 0.72% to 0.9% by weight, based on the total mixture containing the catalyst.

It is important to note that if higher removal of water is desired, the temperature of the mixture containing the catalyst may be lowered, and stripping of water may be conducted at that lower temperature. The lower the temperature of the mixture containing the catalyst, the lower the critical level of water (precipitation water level) at which the catalyst precipitates.

According to the disclosure of the aforementioned patent, removal of the water is conducted after cooling the mixture containing the catalyst, separating the mixture into a polar and non-polar phase, decanting the polar phase containing most of the catalyst and precipitated adipic acid, recycling the non-polar phase back to the reaction chamber, removing the adipic acid from the polar phase, adding cyclohexane to the filtered polar phase, heating the mixture, and stripping off water as an azeotrope with the cyclohexane so that the water level moves to the range of 0.3% to 0.7%.

The disclosed process involves many steps, which may be avoided according to a highly preferred embodiment of the instant invention. According to this highly preferred embodiment, the water removal is conducted before the separation of the intermediate oxidation product, such as adipic acid for example, after determining the appropriate temperature at which the mixture containing the catalyst should be at, and after determining the critical water level at which catalyst precipitates at the temperature of the mixture containing the catalyst. The water level is then maintained at preferable levels as discussed earlier. In a preferred mode of the same embodiment, the intermediate oxidation product, such as adipic acid for example, is precipitated by flash crystallization in one or multiple stages, as discussed later, thus avoiding formation of two liquid phases, need for decantation, etc.

For better clarification of this invention, the examples given below assume that the hydrocarbon is cyclohexane, the intermediate oxidation product is adipic acid, the solvent is acetic acid, and the catalyst is a cobalt compound. It should be understood, however, that the teachings of this invention are applicable to different hydrocarbons, intermediate oxidation products, solvents, and catalysts than the ones used in the examples. Only minor modifications may be needed to fit each individual case.

Figure 1:
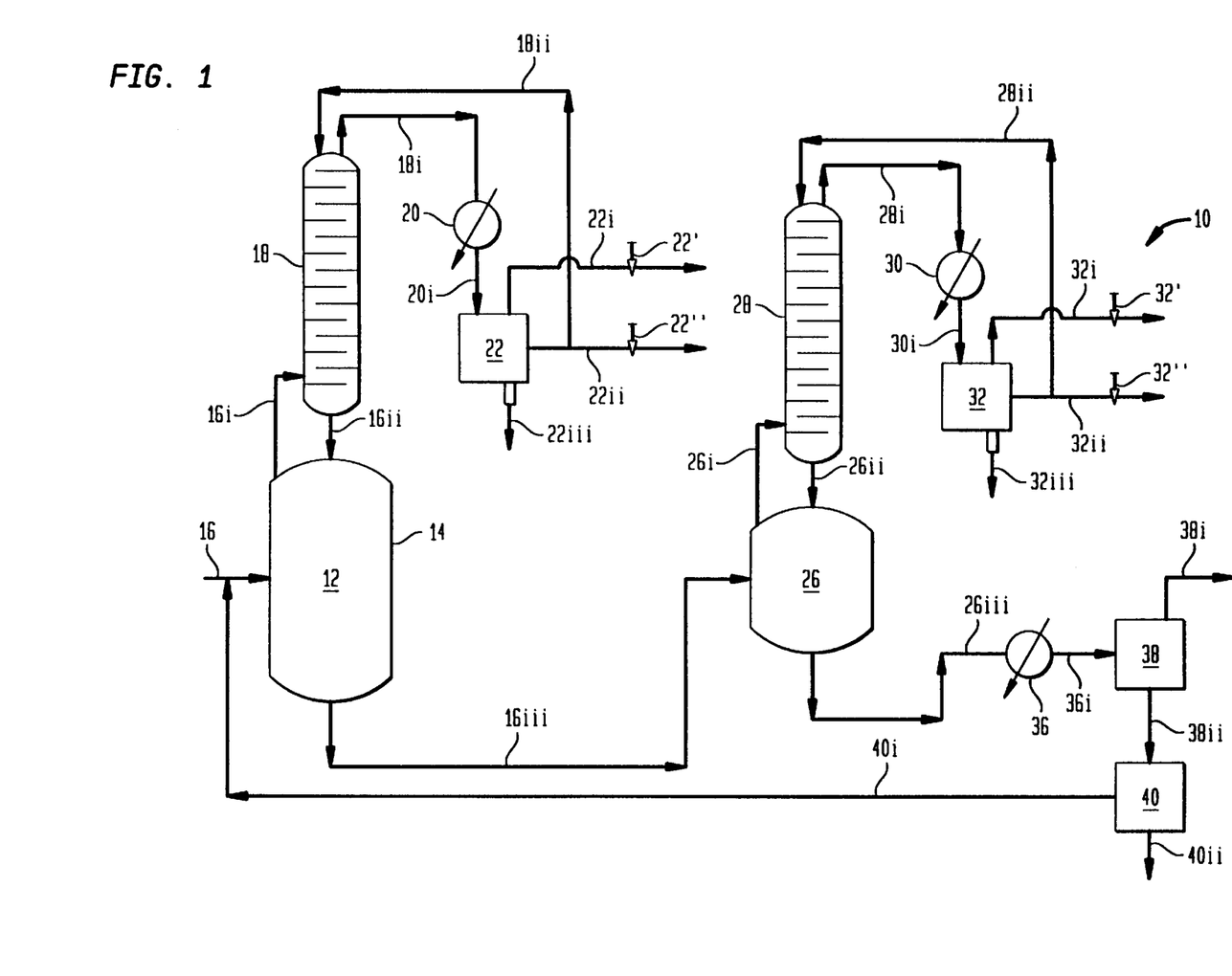
FIG. 1 is a block diagram illustrating a preferred embodiment of the present invention.

Referring now to FIG. 1, there is depicted a reactor system or device 10, comprising a reaction chamber 12 containing a reaction zone 14. The reactor system or device 10 is only partially shown for demonstrating the components necessary to exemplify the present invention. Miscellaneous treatment, product or by-product separation, recycling, etc. devices, well known to the art, are not shown for purposes of clarity and brevity.

Feeding means (for raw materials, miscellaneous recycled matter, gaseous oxidant, etc.) connected to the reaction chamber 12 are represented by a single feeding line 16 for purposes of clarity and brevity. However, it should be understood that, in practice, a number of individual lines may be used, including if appropriate, devices such as for example mixing vessels, heaters, coolers, etc.

Preferably a first distillation column 18 may also be utilized. The first distillation column 18 is connected at one end to the reaction chamber 12 through lines 16$i$ and 16$ii$, while at the other end is connected to a first condenser 20 through line 18$i$. The first condenser 20 is in turn connected to a first decanter 22 through line 20$i$. The first decanter 22 has a first vent line 22$i$, a first cyclohexane (or other hydrocarbon) removal line 22$ii$, and a first water removal line 22$iii$. Lines 22$i$ and 22$ii$ are connected to valves 22' and 22", respectively. Line 22$ii$ is also connected to line 18$ii$ for recycling cyclohexane to the first distillation column 18.

The reaction chamber 12 is also connected to the de-watering chamber 26 through line 16$iii$.

A second distillation column 28 is connected at one end to the de-watering chamber 26 through lines 26$i$ and 26$ii$, while at the other end is connected to a second condenser 30 through line 28$i$. The second condenser 30 is in turn connected to a second decanter 32 through line 30$i$. The second decanter 32 has a second vent line 32$i$, a second cyclohexane (or other hydrocarbon) removal line 32$ii$, and a second water removal line 32$iii$. Lines 32$i$ and 32$ii$ are connected to valves 32' (vent valve) and 32" (hydrocarbon sampling or removal valve), respectively. Line 32$ii$ is also connected to line 28$ii$ for recycling cyclohexane to the second distillation column 28.

The de-watering chamber 26 is also connected through line 26$iii$ to a cooler 36, which in turn is connected to a crystallizer 38 through line 36$i$. The crystallizer 38 is preferably a flash crystallizer, which uses a pressure reduction line 38$i$. The pressure reduction (which may go from the operation pressure to any lower pressure, including sub-atmospheric) in the crystallizer, has as a result a substantially instantaneous drop in temperature, which in turn causes solids (such as adipic acid for example) to crystallize and precipitate. Flashing may be conducted in one or more stages. The crystallizer 38 is connected to a solids separator 40 through line 38$ii$. The crystallized solids are separated and removed from the solids separator 40 through line 40$ii$, while the remaining liquids are removed through line 40$i$, for direct recycling or recycling after further treatment.

In place of the de-watering chamber 26, a re-boiler (not shown) may be used at the bottom of column 28, in which case, line 16$iii$ would be connected at a desired point in column 28. Chamber 26 is useful for containing accidentally precipitated catalyst and prevent plugging of the column.

In operation of this embodiment, miscellaneous raw materials and recyclables, including in this example cyclohexane, acetic acid, cobalt compound catalyst, optional initiator (preferably cyclohexanone or acetaldehyde, or a mixture thereof), optionally water, and a gaseous oxidant, preferably comprising oxygen, enter the reaction zone 14, inside the reaction chamber 12, through the feeding means represented by line 16.

The oxidation is preferably brought to a steady state, and preferably the majority or all the heat of reaction is removed by evaporated condensible matter, which exits the reaction chamber 12 as vapors through line 16$i$, and at least partially returns to the reaction chamber 12 as condensate through line 16$ii$. In this example, the majority of vapors exiting the reaction chamber 12 are cyclohexane, acetic acid, and water. The column 18 is designed, by techniques well known to the art, in a manner that, for all practical purposes, substantially all the acetic acid in the vapors exiting through line 16*i* is condensed in the first column 18 and returns to the reaction chamber 12 through line 16*ii*. For all practical purposes, the majority of the cyclohexane and substantially all the water in the vapors exiting the reaction chamber 12, pass through the first column 18, are condensed in the condenser 20, and are separated in the decanter 22. The condensed cyclohexane is returned to the top of the column 18 through line 18*ii*. As the condensed cyclohexane moves downward, it causes condensation of the acetic acid, and they both return to the reaction chamber 12 through line 16*ii*. An adequate amount of water is preferably recycled, or fresh water added, to the reaction chamber 12, so that the catalyst remains in solution under the operation conditions. At the same time, the amount of water recycled or added should preferably be low enough, so that substantially a single liquid phase is present in the reaction zone 14 of the reaction chamber 12. Formation or existence of a second liquid phase in the reaction zone 14 reduces considerably the reaction rate and reactivity.

Off-gases are removed from line 22*i* through valve 22'. The majority of off-gases comprises mainly non-condensible gases, usually nitrogen, oxygen, carbon dioxide, carbon monoxide, etc. for example, with minor amounts of condensible matter, comprising for example such vapors as cyclohexane, acetic acid, water, etc. Recycling of gases (not shown) from line 22*i* to the reaction chamber 12 is many times desirable in order to improve sparging and mixing, to conserve oxygen, to reduce treatment requirements of the final off-gases, etc.

The valve 22" may be used in order to remove a sample, or part of the cyclohexane, if so desired.

The reaction mixture, having reached a steady state at a predetermined operation temperature, pressure, and desired conversion in the reaction zone 14 of the reaction chamber 12, is preferably continuously being removed from line 16*iii* as a reaction mixture stream. This stream is directed to de-watering means, such as the de-watering chamber 26, for example.

In the case of adipic acid production for example, if the operation temperature in the reaction zone 14 is 100° C. for example, the temperature in the de-watering chamber is brought to a temperature preferably in the range of 70 to 90° C. The temperature in the de-watering chamber 26 is kept in the desired range by provision of heat to it. For example, heat may be provided to the de-watering chamber 26 by heating coils (not shown), inside or outside the de-watering chamber 26, or by circulating at least part of the contents of the chamber 26 through a heater (not shown), or by any other technique well known to the art.

Adding heat to the contents of the de-watering chamber 26 and maintaining the desired temperature is very important in order to continue evaporating cyclohexane, which azeotropically removes water from the contents of the de-watering chamber 26, as the azeotrope passes through the second distillation column 28 in the same manner as already described for the first distillation column 18. The azeotrope of cyclohexane/water is condensed in the condenser 30, and the cyclohexane is separated from the water in the decanter 32. At least part of the cyclohexane is directed back to the to the top of the distillation column 28, and finally returns to the de-watering chamber 26. Removal of cyclohexane, through line 32*ii* for example, helps in attaining a lower water level in the de-watering chamber 26, at a given temperature, without catalyst precipitation.

More than one de-watering chambers with respective distillation columns, and respective or common condensers and decanters may be used, preferably in series for greater removal of water.

A stream containing an amount of water above the critical water level as explained above (and also see comments below) moves through line 26*iii* to an optional cooler 36. The stream may be cooled down either by the cooler 36, or more preferably by flash crystallization in the crystallizer 38, or both. Flash crystallization is conducted by pressure reduction through line 38*i* in one or more stages. During the pressure reduction, cyclohexane and/or acetic acid is evaporated from the mixture, causing drastic temperature drop, so that the intermediate oxidation product, adipic acid in this example, precipitates and forms a slurry, which slurry is transferred, preferably continuously, to the solids separator 40. The adipic acid is removed through line 40*ii*, while the filtrate is removed through line 40*i* for recycling. The cyclohexane which is removed from line 38*i* may be condensed, and preferably also be recycled to the reaction chamber 12 through feeding line 16, with or without pretreatment. The cooler 36 may be used by itself for cooling the mixture or it may be used in conjunction with the flash crystallization process. The cooler 36 may also be part of the crystallizer 38 for further cooling the contents of the crystallizer. Liquid cyclohexane may be introduced to line 36*i* for cooling in the flash crystallizer 38.

Due to the low content of water in the mixture entering the crystallizer 38, and the removal of cyclohexane in the crystallizer, a second liquid phase is not formed under normal circumstances.

It should be pointed out that some water also evaporates along with the cyclohexane due to the reduced pressure in the crystallizer. The amount of water leaving the system may be found experimentally very easily from the vapor stream in line 38*i*, or the condensate of the vapors at a later stage, for example. This amount of water, at the operating temperature of the crystallizer 38, has to be taken into account in determining the amount of water to be removed by the second distillation column 28, so that no catalyst precipitates in the crystallizer 38.

In a different embodiment of the instant invention, the intermediate oxidation product, such as adipic acid for example, may be removed before the removal of water. The operation of this embodiment is very similar to the one discussed above. Preferably, the precipitation of the intermediate oxidation product is conducted in a manner that a single liquid phase is maintained, by flash crystallization for example.

Figure 2:
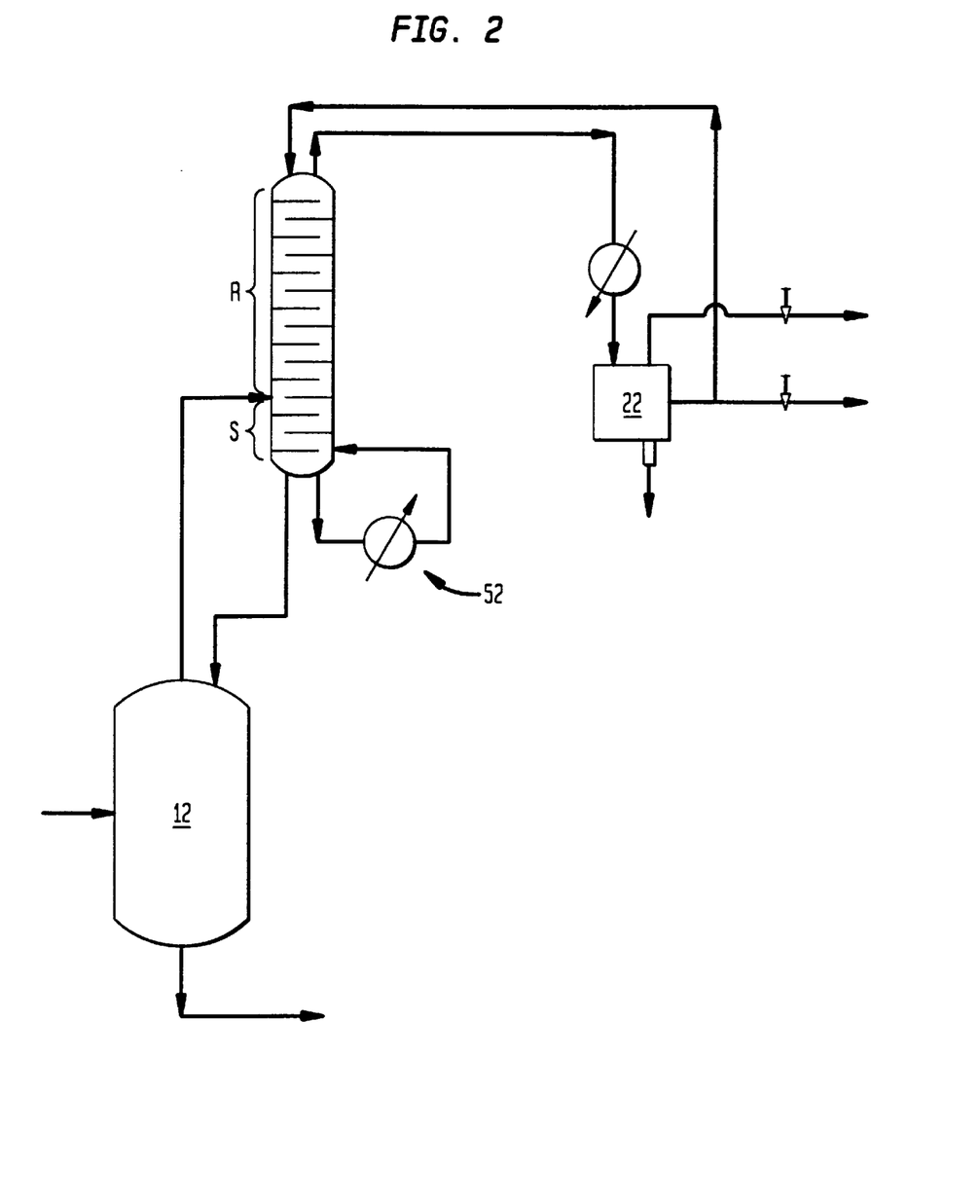
FIG. 2 illustrates a block diagram of a preferred distillation column, which may be used in conjunction with the reaction chamber or the de-watering chamber or any other appropriate chamber, or a combination thereof. This column is provided with a re-boiler, and is divided into a lower stripper zone and an upper rectifier zone.

In the practice of this invention, on many occasions, it is preferable to use one or more distillation columns of the type shown in FIG. 2, which may replace column 18 and/or 28, shown in FIG. 1. The distillation columns of this type are well known to the art. They have a stripper zone S and a rectifier zone R, above the stripper zone, as well as a re-boiler section 52, as shown in FIG. 5. They are characterized by better separation of the constituents entering the column, although they use more energy due to the additional re-boiler.

It should be understood that according to the present invention, any liquids or gases or off-gases may be recycled totally or partially from any section to any other section, if so desired.

Although miscellaneous functions are preferably controlled by a computerized controller, it is possible, according to this invention, to utilize any other type of controller or even manual controls and/or labor for controlling one or more functions. Preferred computerized controllers are artificially intelligent systems (expert systems, neural networks, and fuzzy logic systems, well known to the art). Of the three types of the artificially intelligent systems, the neural network, which is a learning system, collects information from different places of the device (for example pressure, temperature, chemical or other analysis, etc.), stores this information along with the result (pressure drop rate, reaction rate, reactivity, and the like, for example), and is programmed to use this information in the future, along with other data if applicable, to make decisions regarding the action to be at each instance. The expert systems are programmed based on the expertise of experienced human beings. The fuzzy logic systems are based on intuition rules in addition to expertise rules.

Oxidations according to this invention, are non-destructive oxidations, wherein the oxidation product is different than carbon monoxide, carbon dioxide, and a mixture thereof, such as adipic acid for example. Of course, small amounts of these gases may be formed along with the oxidation product, which may be one product or a mixture of products.

Examples include, but of course, are not limited to preparation of $C_5$–$C_8$ aliphatic dibasic acids from the corresponding saturated cycloaliphatic hydrocarbons, such as for example preparation of adipic acid from cyclohexane. Examples of aromatic carboxylic acids are benzoic acid, phthalic acid, isophthalic, and acid terephthalic acid, among others.

Regarding adipic acid, the preparation of which is especially suited to the methods and apparatuses of this invention, general information may be found in a plethora of U.S. Patents, among other references. These, include, but are not limited to: U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); 4,263,453; 4,331,608; 4,606,863; 4,902,827; 5,221,800; and 5,321,157.

Diacids (for example adipic acid, phthalic acid, isophthalic acid, terephthalic acid, and the like) or other suitable compounds may be reacted, according to well known to the art techniques, with a third reactant selected from a group consisting of a polyol, a polyamine, and a polyamide in a manner to form a polymer of a polyester, or a polyamide, or a (polyimide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by well known to the art techniques to form fibers.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of this invention.

We claim:

1. A method of maintaining catalyst in solution after water removal, outside a reaction zone, in a process comprising oxidation of a hydrocarbon by a gaseous oxidant to a respective intermediate oxidation product at an operation temperature in the reaction zone containing a mixture comprising the hydrocarbon, the catalyst, the water, a solvent, and an optional initiator, the method comprising sequential steps of:
   (a) changing, outside the reaction zone, the operation temperature of the mixture to a second temperature below a precipitation temperature, at which and over which precipitation temperature, the catalyst in the first mixture precipitates, at least partially, if the water level in the first mixture is reduced to or under a precipitation water level, while the catalyst in the first mixture remains in solution if the water level in the first mixture is maintained above the precipitation water level;
   (b) removing an amount of water from the first mixture, but maintaining the water level in the mixture over the precipitation water level at the second temperature;
   (c) removing at least part of the intermediate oxidation product; and
   (d) re-circulating the remaining mixture to the reaction zone.

2. A method as defined in claim 1, wherein all steps are conducted at a substantially single liquid phase region.

3. A method as defined in claim 1, wherein step (b) comprises a step of lowering the second temperature to a third temperature lower than the second temperature.

4. A method as defined in claim 2, wherein step (b) comprises a step of lowering the second temperature to a third temperature lower than the second temperature.

5. A method as defined in claim 1, wherein step (c) comprises a step selected from a group consisting of centrifuging, filtering, and a combination thereof.

6. A method as defined in claim 2, wherein step (c) comprises a step selected from a group consisting of centrifuging, filtering, and a combination thereof.

7. A method as defined in claim 3, wherein step (c) comprises a step selected from a group consisting of centrifuging, filtering, and a combination thereof.

8. A method as defined in claim 4, wherein step (c) comprises a step selected from a group consisting of centrifuging, filtering, and a combination thereof.

9. A method as defined in claim 1, wherein step (a) comprises a step of atomizing the first mixture.

10. A method as defined in claim 2, wherein step (a) comprises a step of atomizing the first mixture.

11. A method as defined in claim 4, wherein step (a) comprises a step of atomizing the first mixture.

12. A method as defined in claim 1, wherein the intermediate oxidation product comprises adipic acid, the hydrocarbon comprises cyclohexane, the catalyst comprises a cobalt compound, the gaseous oxidant comprises oxygen, the solvent comprises acetic acid, and the optional initiator is selected from a group comprising cyclohexanone, cyclohexylhydroperoxide, acetaldehyde, and a mixture thereof.

13. A method as defined in claim 2, wherein the intermediate oxidation product comprises adipic acid, the hydrocarbon comprises cyclohexane, the catalyst comprises a cobalt compound, the gaseous oxidant comprises oxygen, the solvent comprises acetic acid, and the optional initiator is selected from a group comprising cyclohexanone, cyclohexylhydroperoxide, acetaldehyde, and a mixture thereof.

14. A method as defined in claim 3, wherein the intermediate oxidation product comprises adipic acid, the hydrocarbon comprises cyclohexane, the catalyst comprises a cobalt compound, the gaseous oxidant comprises oxygen, the solvent comprises acetic acid, and the optional initiator is selected from a group comprising cyclohexanone, cyclohexylhydroperoxide, acetaldehyde, and a mixture thereof.

15. A method as defined in claim 4, wherein the intermediate oxidation product comprises adipic acid, the hydrocarbon comprises cyclohexane, the catalyst comprises a cobalt compound, the gaseous oxidant comprises oxygen, the solvent comprises acetic acid, and the optional initiator is selected from a group comprising cyclohexanone, cyclohexylhydroperoxide, acetaldehyde, and a mixture thereof.

16. A method as defined in claim 5, wherein the intermediate oxidation product comprises adipic acid, the hydrocarbon comprises cyclohexane, the catalyst comprises a cobalt compound, the gaseous oxidant comprises oxygen, the solvent comprises acetic acid, and the optional initiator is selected from a group comprising cyclohexanone, cyclohexylhydroperoxide, acetaldehyde, and a mixture thereof.

17. A method as defined in claim 6, wherein the intermediate oxidation product comprises adipic acid, the hydrocarbon comprises cyclohexane, the catalyst comprises a cobalt compound, the gaseous oxidant comprises oxygen, the solvent comprises acetic acid, and the optional initiator is selected from a group comprising cyclohexanone, cyclohexylhydroperoxide, acetaldehyde, and a mixture thereof.

18. A method as defined in claim 7, wherein the intermediate oxidation product comprises adipic acid, the hydrocarbon comprises cyclohexane, the catalyst comprises a cobalt compound, the gaseous oxidant comprises oxygen, the solvent comprises acetic acid, and the optional initiator is selected from a group comprising cyclohexanone, cyclohexylhydroperoxide, acetaldehyde, and a mixture thereof.

19. A method as defined in claim 8, wherein the intermediate oxidation product comprises adipic acid, the hydrocarbon comprises cyclohexane, the catalyst comprises a cobalt compound, the gaseous oxidant comprises oxygen, the solvent comprises acetic acid, and the optional initiator is selected from a group comprising cyclohexanone, cyclohexylhydroperoxide, acetaldehyde, and a mixture thereof.

20. A method as defined in claim 9, wherein the intermediate oxidation product comprises adipic acid, the hydrocarbon comprises cyclohexane, the catalyst comprises a cobalt compound, the gaseous oxidant comprises oxygen, the solvent comprises acetic acid, and the optional initiator is selected from a group comprising cyclohexanone, cyclohexylhydroperoxide, acetaldehyde, and a mixture thereof.

21. A method as defined in claim 10, wherein the intermediate oxidation product comprises adipic acid, the hydrocarbon comprises cyclohexane, the catalyst comprises a cobalt compound, the gaseous oxidant comprises oxygen, the solvent comprises acetic acid, and the optional initiator is selected from a group comprising cyclohexanone, cyclohexylhydroperoxide, acetaldehyde, and a mixture thereof.

22. A method as defined in claim 11, wherein the intermediate oxidation product comprises adipic acid, the hydrocarbon comprises cyclohexane, the catalyst comprises a cobalt compound, the gaseous oxidant comprises oxygen, the solvent comprises acetic acid, and the optional initiator is selected from a group comprising cyclohexanone, cyclohexylhydroperoxide, acetaldehyde, and a mixture thereof.

23. A method of maintaining catalyst in solution for recycling after water removal, outside a reaction zone, in a process comprising oxidation of a hydrocarbon by a gaseous oxidant to a respective intermediate oxidation product at an operation temperature in the reaction zone containing a mixture comprising the hydrocarbon, the catalyst, the water, a solvent, and an optional initiator, the method comprising steps of:

(e) precipitating at least partially the intermediate oxidation product, while maintaining a single liquid phase;

(f) removing at least part of the precipitated intermediate oxidation product;

(g) removing part of the water at a temperature below a precipitation temperature, at which and over which precipitation temperature, the catalyst in the mixture would precipitate, at least partially, if the water level in the mixture had been reduced to or under a precipitation water level;

(h) maintaining the water level over the precipitation water level; and (i) recycling at least part of a mixture created in step (h) back to the reaction zone.

24. A method as defined in claim 23, wherein the intermediate oxidation product comprises adipic acid, the hydrocarbon comprises cyclohexane, the catalyst comprises a cobalt compound, the gaseous oxidant comprises oxygen, the solvent comprises acetic acid, and the optional initiator is selected from a group comprising cyclohexanone, cyclohexylhydroperoxide, acetaldehyde, and a mixture thereof.

25. A method as defined in claim 1, wherein the intermediate oxidation product comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

26. A method as defined in claim 25, further comprising a step of spinning the polymer into fibers.

27. A method as defined in claim 2, wherein the intermediate oxidation product comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

28. A method as defined in claim 27, further comprising a step of spinning the polymer into fibers.

29. A method as defined in claim 3, wherein the intermediate oxidation product comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

30. A method as defined in claim 29, further comprising a step of spinning the polymer into fibers.

31. A method as defined in claim 4, wherein the intermediate oxidation product comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

32. A method as defined in claim 31, further comprising a step of spinning the polymer into fibers.

33. A method as defined in claim 9, wherein the intermediate oxidation product comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

34. A method as defined in claim 33, further comprising a step of spinning the polymer into fibers.

35. A method as defined in claim 10, wherein the intermediate oxidation product comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

36. A method as defined in claim 35, further comprising a step of spinning the polymer into fibers.

37. A method as defined in claim 23, wherein the intermediate oxidation product comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

38. A method as defined in claim 37, further comprising a step of spinning the polymer into fibers.

\* \* \* \* \*